(12) United States Patent
Smith et al.

(10) Patent No.: US 10,928,371 B1
(45) Date of Patent: Feb. 23, 2021

(54) HAND-HELD SENSOR AND MONITOR SYSTEM

(71) Applicant: Air Stations LLC/Elevated Analytics LLC Joint Venture, Tulsa, OK (US)

(72) Inventors: Joseph D. Smith, Rolla, MO (US); Robert E. Jackson, Mapleton, UT (US); Zachary P. Smith, Broken Arrow, OK (US)

(73) Assignee: AIR STATIONS LLC/ELEVATED ANALYTICS LLC JOINT VENTURE, Tulsa, OK (US)

( * ) Notice: Subject to any disclaimer, the term of this patent is extended or adjusted under 35 U.S.C. 154(b) by 172 days.

(21) Appl. No.: 15/933,997

(22) Filed: Mar. 23, 2018

Related U.S. Application Data (60) Provisional application No. 62/479,846, filed on Mar. 31, 2017.

(51) Int. Cl.
| | | |
|---|---|---|
| *G01N 33/00* | (2006.01) | |
| *G01N 15/06* | (2006.01) | |
| *G08B 21/12* | (2006.01) | |

(52) U.S. Cl.
CPC ..... *G01N 33/0062* (2013.01); *G01N 15/0606* (2013.01); *G01N 33/0063* (2013.01); *G01N 2033/0068* (2013.01); *G08B 21/12* (2013.01)

(58) Field of Classification Search
CPC ........... G01N 33/0062; G01N 33/0063; G01N 15/0606; G01N 2033/0068; G08B 21/12
See application file for complete search history.

(56) References Cited

U.S. PATENT DOCUMENTS

| | | | |
|---|---|---|---|
| 5,831,876 A | 11/1998 | Orr et al. | |
| 6,085,576 A | 7/2000 | Sunshine et al. | |
| 6,941,193 B2 * | 9/2005 | Frecska | G05B 15/02 |
| | | | 700/276 |
| 7,259,357 B2 | 8/2007 | Walker | |
| 7,360,461 B2 | 4/2008 | Desrochers et al. | |

(Continued)

FOREIGN PATENT DOCUMENTS

| | | |
|---|---|---|
| CN | 202083808 | 12/2011 |
| CN | 103728198 | 4/2014 |

(Continued)

OTHER PUBLICATIONS

David T. Allen, Vincent M. Torres, TCEQ 2010 Flare Study Final Report, Texas Commission on Environmental Quality, The University of Texas at Austin the Center for Energy and Environmental Resources, Aug. 1, 2011.

(Continued)

*Primary Examiner* — Suman K Nath
(74) *Attorney, Agent, or Firm* — Head, Johnson, Kachigian & Wilkinson, PC (57) ABSTRACT

A hand-held sensor and monitor system for sensing and monitoring atmospheric air quality. The system includes a plurality of sensors and a microcontroller in communication with the plurality of sensors to receive data therefrom. A mobile electronic device is in communication with the microcontroller and is capable of receiving data from the microcontroller. The plurality of sensors and the microcontroller are either integrated within the mobile electronic device or are attachable to and detachable from the mobile electronic device.

20 Claims, 5 Drawing Sheets

(56) References Cited

U.S. PATENT DOCUMENTS

| | | | |
|---|---|---|---|
| 8,765,488 | B2 | 7/2014 | Strano et al. |
| 8,955,367 | B2 | 2/2015 | Gouma et al. |
| 9,199,725 | B2 | 12/2015 | Yelland et al. |
| 9,311,805 | B2 | 4/2016 | Zishaan |
| 9,405,533 | B2 | 8/2016 | Bouzas et al. |
| 9,453,814 | B2 | 9/2016 | Tran |
| 9,536,149 | B1 | 1/2017 | Cesarano |
| 9,551,616 | B2 | 1/2017 | McQuilkin et al. |
| 2005/0139363 | A1 | 6/2005 | Thomas |
| 2005/0262943 | A1 | 12/2005 | Claydon et al. |
| 2006/0000259 | A1 | 1/2006 | Rothschild et al. |
| 2007/0005267 | A1 | 1/2007 | Li |
| 2007/0232950 | A1 | 10/2007 | West |
| 2009/0100458 | A1 | 4/2009 | Chan et al. |
| 2010/0225493 | A1 | 9/2010 | Zishaan |
| 2011/0051775 | A1 | 3/2011 | Ivanov et al. |
| 2011/0174054 | A1 | 7/2011 | Lynn |
| 2012/0015621 | A1 | 1/2012 | Cerny et al. |
| 2012/0326093 | A1 | 12/2012 | Landorf |
| 2014/0138588 | A1 | 5/2014 | Landorf et al. |
| 2014/0228698 | A1* | 8/2014 | Roeck .................. G01N 33/497 600/532 |
| 2014/0315323 | A1 | 10/2014 | Pereira et al. |
| 2016/0025517 | A1 | 1/2016 | Giedd et al. |
| 2017/0016850 | A1 | 1/2017 | Tran |
| 2017/0272338 | A1* | 9/2017 | Borrel .................. H04W 4/023 |

FOREIGN PATENT DOCUMENTS

| | | |
|---|---|---|
| CN | 104458905 | 3/2015 |
| CN | 104583764 | 4/2015 |
| CN | 104713922 | 6/2015 |
| CN | 204557260 | 8/2015 |
| CN | 204719251 | 10/2015 |
| CN | 105051658 | 11/2015 |
| CN | 204901580 U | 12/2015 |
| CN | 204964476 | 1/2016 |
| CN | 106168617 | 11/2016 |
| EP | 527307 | 2/1993 |
| EP | 2048854 | 4/2009 |
| EP | 2304427 | 4/2011 |
| EP | 2699888 | 2/2014 |
| EP | 3092540 | 11/2016 |
| EP | 2761285 | 2/2017 |
| EP | 3183722 | 6/2017 |
| KR | 1020110077040 | 7/2011 |
| KR | 1020150112118 | 10/2015 |
| NZ | 566000 | 4/2011 |
| WO | 2009013508 | 1/2009 |
| WO | 2010013023 | 2/2010 |
| WO | 2010037425 | 4/2010 |
| WO | 2012023136 | 2/2012 |
| WO | 2012177975 | 12/2012 |
| WO | 2013112287 | 8/2013 |
| WO | 2014081331 | 5/2014 |
| WO | 2016145300 | 9/2016 |
| WO | 2016147098 | 9/2016 |
| WO | 2017068499 | 4/2017 |

OTHER PUBLICATIONS

Kelsey D. Atherton, NASA Now Has a Drone That Can Sniff Out Dangerous Gas Leaks, Popular Science, Mar. 30, 2016.
Black Swift Technologies, Commercial & Scientific Unmanned Aircraft, http://blackswifttech.com/, 2017.
Christophe Buchler, Magali Rollin, User-Friendly Composites That Take the Heat, JEC Magazine, Nov.-Dec. 2009, p. 33-35, No. 53.
Shay Castle, Boulder's Black Swift Wins NASA Deal for Drone-Based Volcano Tracking, Boulder Daily Camera, May 3, 2017.
Dennis Fandrich, Mark Iden, Drones with Innovative Gas Detection Sensors Usher in a New Pipeline Inspection Era, Pipeline Technology Journal, Mar. 30, 2016.
Luke Geiver, GE Unveils Drone, Sensor Package Aimed at Detecting Fugitive Gas, UAS Magazine, Oct. 12, 2016.
Dr. Felipe Gonzalez, Miguel A. Alvarado Molina, Tommaso Villa, UAVs for Gas Plume and Ultrafine Particles Monitoring, Mining and Energy in 2025 & Beyond, May 26, 2016.
GPS World Staff, Inspector Gadget: Drones Could Solve Gas-Leak Detection Issue, GPS World, Mar. 5, 2016.
Matthew R. Johnson, Robin W. Devillers, Kevin A. Thomson, Quantitative Field Measurement of Soot Emission from a Large Gas Flare Using Sky-LOSA, Environmental Science and Technology, 2011, vol. 45. p. 345-350.
Matthew R. Johnson, Robin W. Devillers, Chen Yang, Keven A. Thomson, Sky-Scattered Solar Radiation Based Plume Transmissivity Measurement to Quantify Soot Emissions from Flares, Enviromental Science and Technology, Sep. 23, 2010, vol. 44, No. 21, p. 8196-8202.
R. Colin Johnson, Gas Sensors Penetrate Smartphones, EE Times, Nov. 5, 2015, AspenCore.
Marc McDaniel, Flare Efficiency Study, Engineering-Science, Inc., Jul. 1983.
James D.N. McEwen, Matthew R. Johnson, Black Carbon Particulate Matter Emission Factors for Buoyancy-Driven Associated Gas Flares, Journal of the Air & Waste Management Association, Jan. 20, 2012.
Mariella Moon, GE Made an Oilfield Drone That Can Sniff Out Gas Leaks, Engadget, Oct. 9, 2016.
Rhett Morgan, Zeeco Calls Its New Direct Flare-Monitoring Technology a Game-Changer, Tulsa World, Jul. 28, 2017.
NASA, Carbon Nanotube Sensors for Gas Detection, Ames Technology Capabilities and Facilities, NASA.gov, Jul. 18, 2016.
NASA, NASA Flies Dragon Eye Unmanned Aircraft Into Volcanic Plume, www.nasa.gov, Apr. 2, 2013.
NASA, Mini NASA Methane Sensor Makes Successful Flight Test, Jet Propulsion Laboratory California Institute of Technology, Mar. 28, 2016.
National Aeronautics and Space Administratioin (NASA), NASA Ames Scientist Develops Cell Phone Chemical Sensor, NASA.gov, Oct. 30, 2009.
Mark Scott, Energy Giants Turn to Drones and Sensors in New Embrace of the Digital World, The New York Times, Nov. 3, 2016, The New York Times Company.
URS Corporation, Passive FTIR Phase I Testing of Simulated and Controlled Flare Systems Final Report, Texas Commission on Environmental Quality, Jun. 2004.
U.S. EPA Office of Air Quality Planning and Standards (OAQPS), Parameters for Properly Designed and Operated Flares, Report for Flare Review Panel, Apr. 2012.
VTT Technical Research Centre of Finland, Scientists Developed a Miniature Gas Sensor for Mobile Devices—Applications from Monitoring Air Quality to Healthcare & Wellness, vttresearch.com, Aug. 13, 2015.

* cited by examiner

HAND-HELD SENSOR AND MONITOR SYSTEM

CROSS-REFERENCE

This application claims priority to and the benefit of U.S. Provisional Patent Application Ser. No. 62/479,846, filed Mar. 31, 2017, which is incorporated herein in its entirety by reference.

BACKGROUND OF THE INVENTION

Field of the Invention

The present invention is directed to a hand-held sensor and monitor system for sensing and monitoring atmospheric air quality. In particular, the present invention is directed to a sensor and monitor system for sensing, monitoring and quantifying atmospheric air conditions surrounding a mobile electronic device and for operating in conjunction with other sensor and monitor systems.

Description of the Related Art

Determining real-time atmospheric and air quality conditions, such as temperature, barometric pressure, and gas concentrations of different gases, including flammable gases, pollutants or toxic compounds, is important for individual health and safety. Examples of the use of the present invention would be as a replacement for an individual hazardous chemical warning device, or as a general air quality monitor for an individual with a special condition, such as asthma.

Chemical plants, petroleum refineries, and other industrial facilities where hazardous chemicals are present sometimes require humans within the plant to carry some sort of monitoring device to determine if the individual has been exposed to specific hazardous substances. This can be as simple as a badge which changes color if exposed to the hazardous substance, or it can be a more complicated detection device, such as a mining gas detection device, which gives more detailed information, such as exposure levels and durations. An example of a more complicated device is the one disclosed in Sunshine et al (U.S. Pat. No. 6,085,576). The more advanced devices are often very costly, ranging from about the same price as a typical smartphone to 5 or 6 times the cost of a phone. Smartphones have become common place and linking the ability to use the smartphone as a replacement for individual monitoring systems would be more cost effective than specialized complicated monitoring devices, plus smartphone-based devices could provide more detailed information than simple exposure badges, with very little additional expense.

The present invention can be tailored to monitor many different gaseous compounds, including specific hazardous compounds in a plant, mine, or other work area. The sensors are small enough to be included inside a mobile electronic device, such as a smartphone or hand-held radio, or could be included in a small separate package that could be linked or docked to the smartphone through the smartphone's USB connection or through a wireless connection, such as Bluetooth™. The sensor data would be monitored by a mobile electronic device software application providing audible warnings, as well as screen displays of hazardous gas concentration levels, and the data could also be stored for later analysis and/or it could be transmitted to a plant safety office computer server for documenting individual safety records and to alert others of potential hazardous conditions.

There are currently advanced hand-held gas sensor devices available on the market. Many of these available products now incorporate wireless transmission capability; however, these devices, in addition to being costly, are typically limited to only the gas sensing function. The current invention provides the same gas sensing capabilities coupled with mobile phone functionality, which provides increased reporting and transmitting functionality, so that data available from the gas sensors can be available not only to the individual with the hand-held device but can be made available to networked work groups or even to the public at large.

Figure 5:
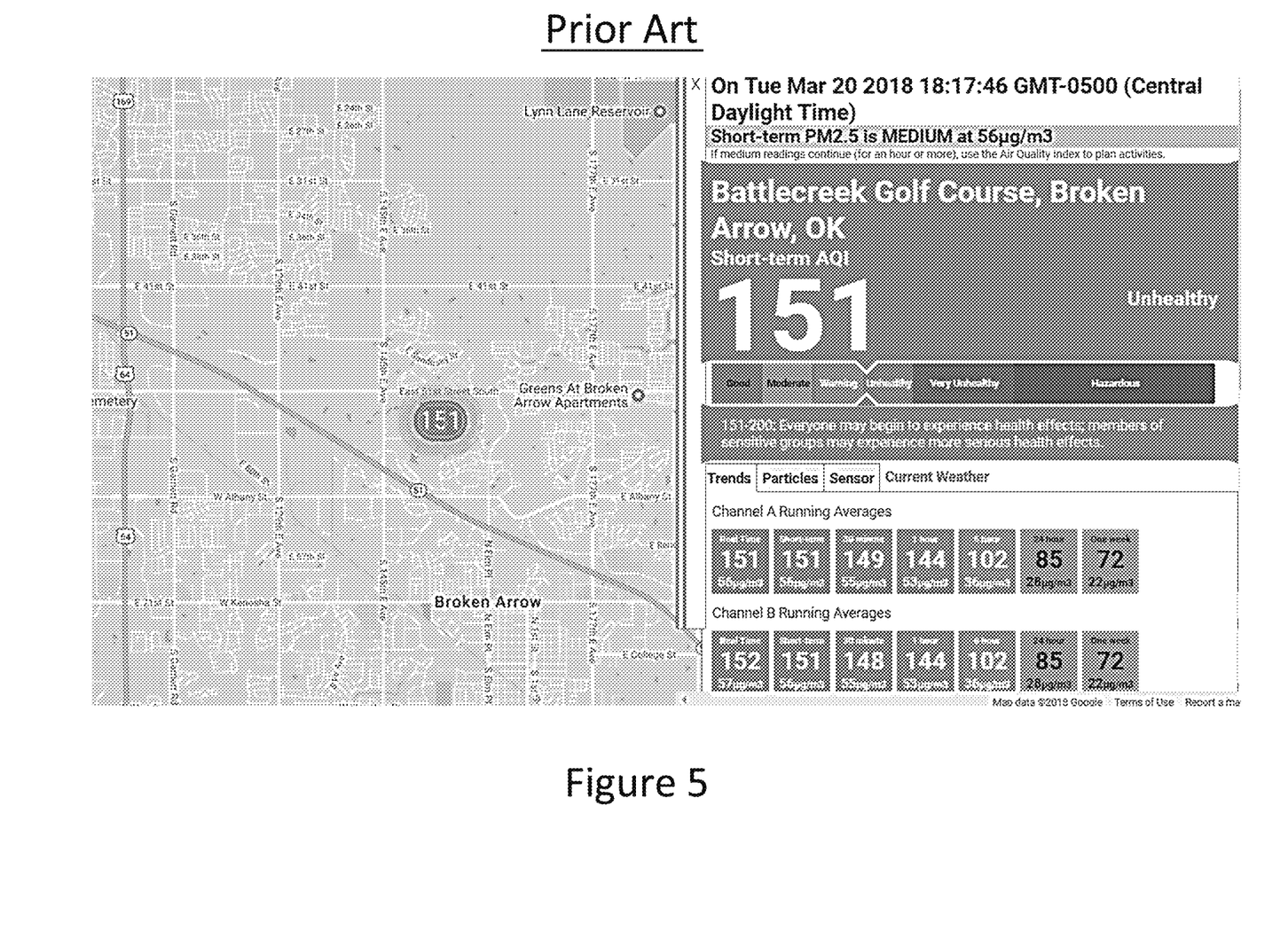
FIG. 5 illustrates an existing map display of air quality and atmospheric conditions.

Many individuals are concerned about the air quality in their neighborhoods. The present invention can also be used by the general public to monitor air quality and atmospheric conditions in their immediate locale. Many individuals have specific conditions, such as asthma, that require careful planning of activities based on the current air quality. The present invention will make it affordable for these individuals to have a continuous monitor always with them in the form of their smartphone, which they already usually carry. Each individual phone-based sensor device could transmit its data to a central computer or server, which could integrate the data and send data back to each phone in the form of a map showing local conditions throughout their community or region (see for example FIG. 5), allowing users to avoid potential hazardous regions. This collated information could then be used by individuals to plan activities, such as outdoor exercise or family outings. The atmospheric temperature, pressure, and humidity conditions could also be monitored and transmitted to the central computer/server, providing additional weather information which could be incorporated into community warning systems, such as tornado warning systems.

The "air quality map" concept would work similar to other mapping applications. A phone application (app) would be developed that would provide a satellite image or a street view showing real-time air quality data plotted in a color contour on a map. The app would provide warnings if local air quality exceeded a pre-determined "safe" level and would provide advice on how to avoid regions of "unhealthy air". This would include a predictive feature that would link local weather conditions (i.e., wind, rain, etc.) and the phone's GPS location data with cloud-based software to predict how air quality may change over a set period of time to advise a user how to avoid hazardous air with a suggested route for the user to go to be safe. This predictive feature could also be used as an early warning to users in the event of a hazardous chemical release and/or alert users of a potential hazard created by an emission source and current atmospheric conditions in a region. This tool may also be used to identify sources of poor air quality in a region which may impact local property values. The mapping feature in the mobile phone air quality app could easily be combined with other apps, such as Google Maps, to show a top-down high-resolution view of cities.

There have been medically oriented gas sensing devices made available, such as those disclosed in Gouma et al (U.S. Pat. No. 8,955,367) and West (U.S. Pat. Publ. No. 2007/0232950) but these devices are intended more for sampling the exhaled breath from individuals to help determine the condition of the individual. These types of devices don't provide information for the individual regarding their surrounding air quality.

In another example, many individuals have specific concerns about indoor air quality. They may work in an environment where aromas or other allergens bother them. Many businesses will hire experts or risk management personnel to do periodic sampling, but few do continuous sampling. The present invention greatly enhances workplace comfort for these individuals by monitoring indoor air quality continuously with sensors tailored to specific indoor quality concerns, such as VOCs. The data could be stored and then provided for documentation when problems or complaints occur. For an office building, the data could be transmitted to an HVAC control system to help adjust the HVAC operation when needed, such as when $CO_2$ levels get too high in a conference room, the HVAC controls would automatically adjust to supply more fresh air to that specific room. Current state of the art includes sensing devices that can monitor indoor air quality, such as the device by Bischel (U.S. Pat. No. 6,941,193) but these are typically limited to stationary devices mounted in the room or the air-return ducting. The present invention would not replace these fixed station devices but would add the functionality of determining conditions throughout the room and the whole building. Having multiple hand-held devices reporting data to the control system would thus improve the operation of the whole HVAC system.

Zishaan (U.S. Pat. Publ. No. 2010/0225493) proposed a hand-held air quality sensing device which would be incorporated into a mobile phone. Applicant also acknowledges the prior art listed by Zishaan, which include: U.S. Pat. No. 4,178,592; GB 2404459; U.S. Pat. Nos. 4,365,237; 5,594,422; 4,968,975; 5,726,634; U.S. Pat. Publ. No. 2002/126016; WO 93/22752; GB 2324398; U.S. Pat. Nos. 5,159,315; 6,462,660; U.S. Pat. Publ. No. 2004/119600; EP 1441300; U.S. Pat. Publ. No. 2006/258407; U.S. Pat. Nos. 5,894,275; 5,801,629; 6,104,288; GB 2400959; WO 99/02987; and EP 0995115.

Zishaan's device, and the prior art he refers to, relates primarily to alarms based on, for example, carbon monoxide or smoke exceeding certain levels. Zishaan incorporates sensors, CO and $CO_2$ sensors are specifically mentioned, and a microcontroller that will monitor the levels of gases and set off alarms when predetermined levels are reached. Thus, Zishaan's phone device would be geared to a more qualitative alarm device rather than the full quantitative device of the present invention. The present invention does not attempt to duplicate the alarming function but would continually sense real-time levels of air quality gases and report the levels measured to the hand-held device as well as transmitting this same data to centrally located specialty servers or to cloud servers as desired.

The present invention is based on small, low-cost microcircuit sensors, such as MEMS-based sensors or carbon nanotube (CNT-based) or equivalent type micro to nanoscale sensors. This new generation of nanoscale sensors has shown great promise for reducing the size, cost and weight of sensors that can determine various properties in gases and liquids [1], [2], [3], [4]. Combining advanced sensor-based technological developments together with a hand-held mobile electronic device, such as a smartphone or its equivalent, enables the present invention.

SUMMARY OF THE INVENTION

The present invention is directed to a hand-held sensor and monitor system for sensing and monitoring atmospheric air quality. The present invention is also directed to a hand-held sensor and monitoring system operating in conjunction with other sensors and monitors to plot and predict air quality.

A plurality of sensors (such as CNT, MEMS, etc.) measure various gaseous concentrations, temperature and humidity. A microcontroller in communication with the plurality of sensors receives data from the sensors. A mobile electronic device is in communication with the microcontroller and is capable of receiving data from the microcontroller. Sensor data may be integrated with and coordinated with map information or general areawide information.

The plurality of sensors and the microcontroller may be integrated into and within the mobile electronic device in one embodiment.

The plurality of sensors and the microcontroller may be attachable to and detachable from the mobile electronic device in another embodiment.

In yet another embodiment, the plurality of sensors and the microcontroller are in wireless communication with the mobile electronic device.

DETAILED DESCRIPTION OF THE INVENTION

The embodiments discussed herein are merely illustrative of specific manners in which to make and use the invention and are not to be interpreted as limiting the scope.

While the invention has been described with a certain degree of particularity, it is to be noted that many modifications may be made in the details of the invention's construction and the arrangement of its components without departing from the scope of this disclosure. It is understood that the invention is not limited to the embodiments set forth herein for purposes of exemplification.

Figure 1:
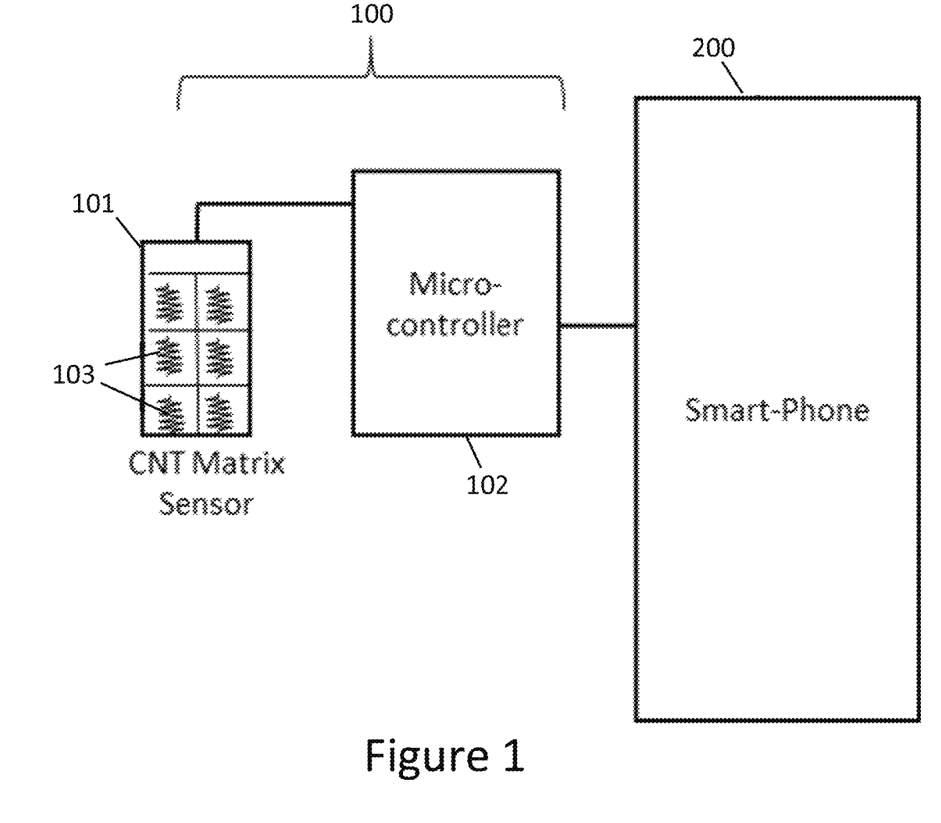
FIG. 1 is a simplified schematic diagram of a hand-held sensor and monitor system for sensing and monitoring atmospheric air quality constructed in accordance with the present invention.

Referring to the drawings in detail, FIG. 1 illustrates a simplified schematic of a hand-held sensor and monitor system in accordance with the present invention. The invention 100 includes a sensor unit 101 that has a matrix or plurality of sensing elements 103 allowing for measurement of multiple parameters, including, but not limited to, temperature, pressure, relative humidity and various gas concentrations. A plurality of electrically interconnected sensors are mounted on a rigid substrate. A power source provides substantially constant current to the electrically interconnected sensors.

Sensors and transducers comprising a thin, electronically "active" sensing layer within a dielectric and/or metallic layered structure may be utilized. The electronic resistance of the active sensing layer is measured during a change in the sensor environment. By utilizing a multi-layered architecture around the active sensing layer, the electronic signal of the sensing element can be improved. By carefully selecting the architecture and materials that surround the active sensing layer, the sensitivity, stability, and selectivity of the sensor to detect changes in the environment are improved. This allows for a number of specific application areas for environmental sensing. Novel transducers can be incorporated into conventional sensor technology, as well as methods of using those transducers to detect the existence of a certain condition, such as a change in temperature or the presence of an analyte. Typical analytes that might be detected include those selected from the group consisting of humidity, gas, airflow, volatile organic compounds (VOCs such as amides, aldehydes, ethers, ketones, esters, and alcohols), and combinations of the foregoing. Advantageously, the present invention is particularly useful for detecting polar VOCs.

In one non-limiting embodiment, the material used to form the active sensing layer is a nanoscale-based material, such as carbon nanotubes (CNT), that can be provided as a thin surface which can react rapidly to changes in electrical properties of the surface as the surface interacts with different gas species. Additionally, the nanotube surface may have the ability to be heated in order to refresh the surface by desorbing the adsorbed gas layer or to increase the sensitivity of the sensing layer for a specific gas or gases and help differentiate between gases. In another non-limiting embodiment, the sensor is composed of nanoscale to microscale materials that comprise a structure, the mechanical properties of which change as gases interact with that structure and in which the structural properties can be measured through an electrical interface. Suitable materials for the active sensing layer or nanostructure include CNT, CNT fabric, carbon film, pyrolytic carbon, graphite, graphene, carbon fiber, carbon soot, carbon black, silicon, and like materials. The sensing layer or structure may also be metal-particle-doped or metal-oxide-doped to enhance sensitivity to various gases.

The resistance or capacitance of the electrically interconnected sensors have a linear response and may be correlated to temperature, pressure, relative humidity, and gaseous concentrations.

The sensor unit 101 is in communication with and controlled by a microcontroller 102. The sensor unit 101 and the microcontroller 102 obtain and receive data on various multiple parameters frequently, up to four times per second.

Figure 2:
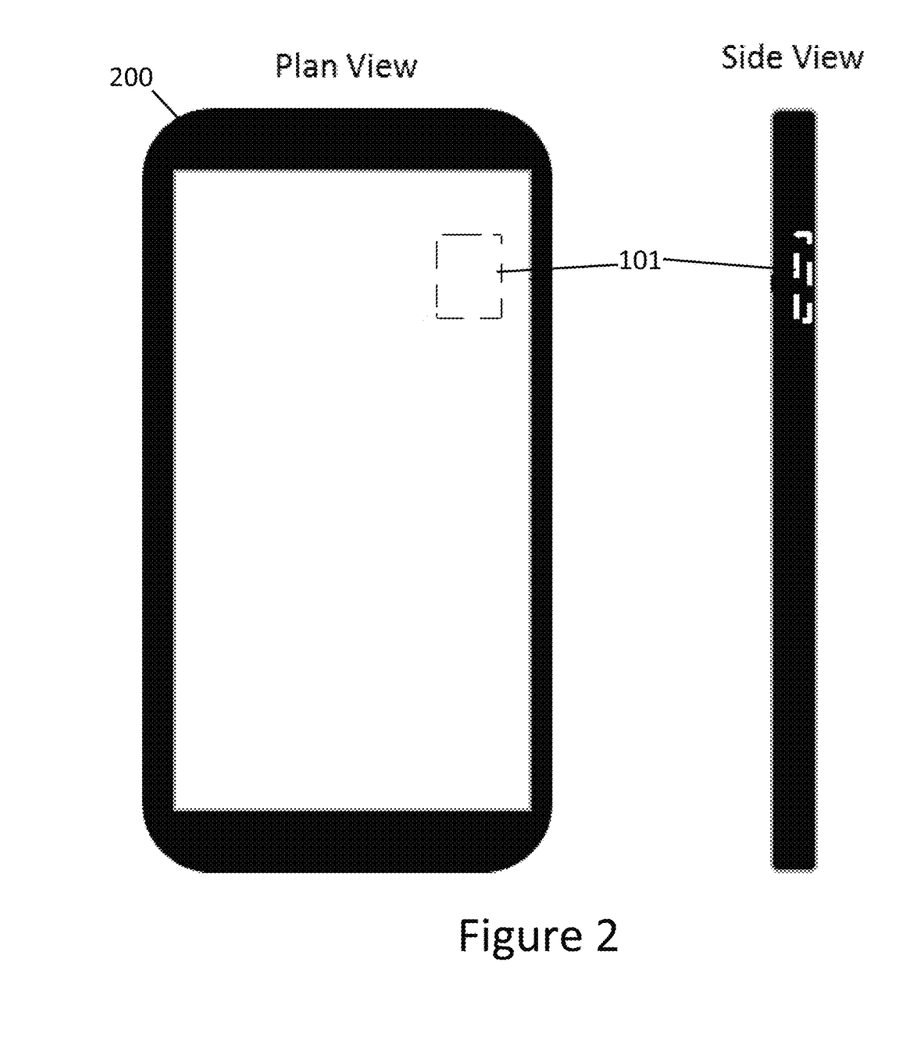
FIG. 2 illustrates a simple graphic plan view and side view of a hand-held sensor and monitor system integrated into a mobile electronic device, such as a cell phone or smartphone.

As seen in the simplified diagram in FIG. 2, the sensor unit 101 is integrated into and contained within a mobile electronic device, such as a smartphone 200. The battery of the mobile electronic device 200 will power the microcontroller.

Figure 3:
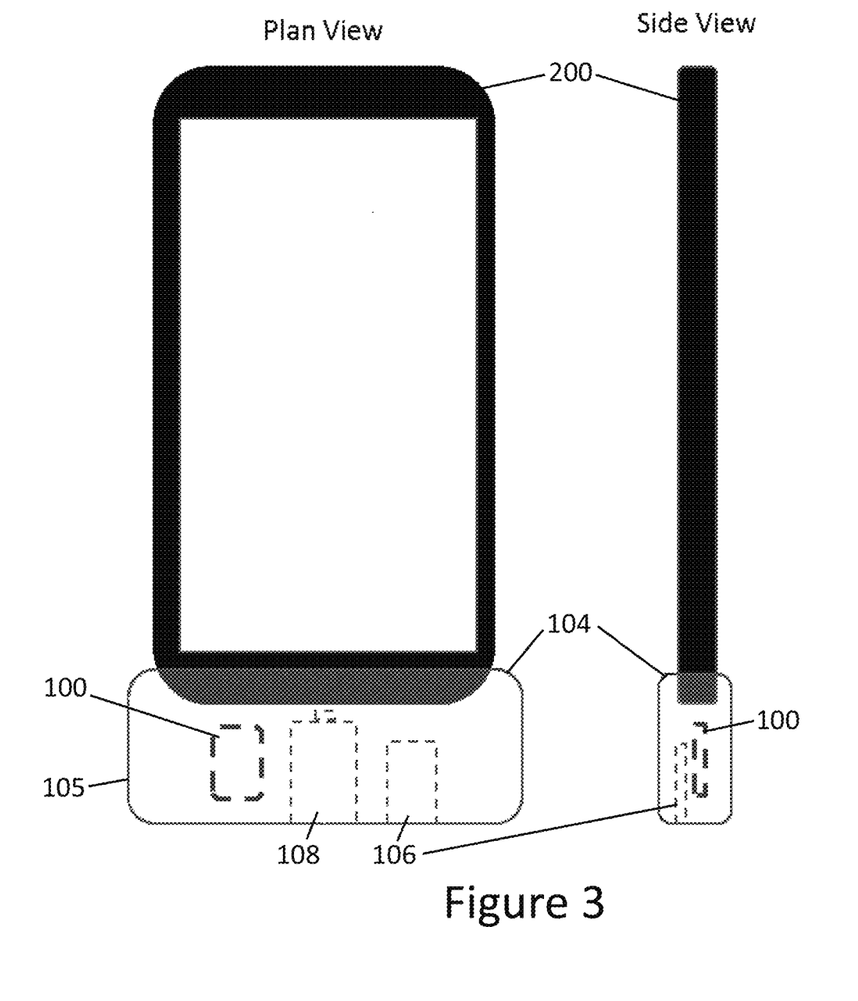
FIG. 3 illustrates a plan view and a side view of an alternate embodiment of a hand-held sensor and monitor system which is attachable to and detachable from a mobile electronic device, such as a cell phone or smartphone.

A further preferred embodiment of the present invention is illustrated in FIG. 3. A sensor package 105 may include the sensor unit 101, including a separate memory storage device 106, such as a micro SD card. A separate battery 108 might also be included to power the sensor unit independent from the mobile device battery. The sensor package 105 would be attachable to and detachable from the mobile electronic device. This might be in the form of a docking system 104.

Figure 4:
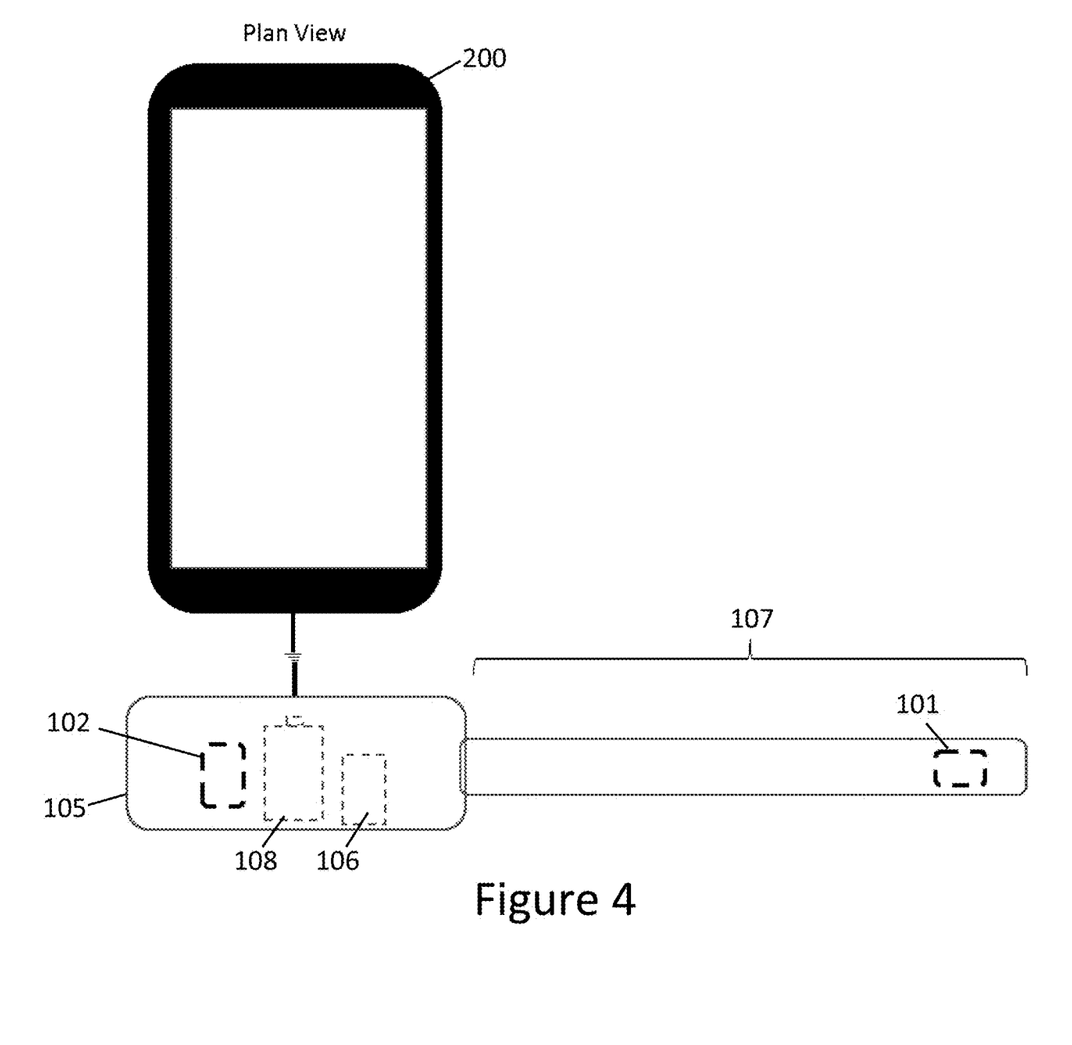
FIG. 4 illustrates a plan view and a side view of a yet further embodiment of a hand-held sensor and monitor system in wireless communication with a mobile electronic device.

In yet a further preferred embodiment illustrated in FIG. 4, the sensor package 105 could be physically separate from the mobile electronic device, but communicate through a wireless connection, such as Bluetooth™ or Wi-Fi. As a further option, the separated sensor package 105 could be in operation separate from the mobile electronic device or physically docked to the mobile electronic device 200. In one configuration, the sensor unit 101 may be located in a wand 107.

The present invention generally relates to the inclusion of various air quality sensors into a hand-held mobile electronic device, such as a smartphone or hand-held radio, or as an attachment that would be connected to a smartphone. The sensors are small enough (on the order of 0.5 inches×0.5 inches×0.01 inches thick), so they can be integrated in a smartphone housing or could be included in a separate housing that is connected to the smartphone via a standard USB type connection. The various sensors will be able to measure temperature, pressure, relative humidity, and various gas concentrations, such as, but not limited to, CO, $CH_4$, $O_2$, and $CO_2$. The sensors will be a quick response sensor capable of responses on the order of 4 samples per second. The sensor package interfaces with the smartphone either directly for smartphone installed sensor systems, or through a direct connection, such as a standard USB type connection, for an embodiment where the sensor package is docked to the smartphone, or through a wireless connection (e.g., Bluetooth™, Wi-Fi) if the sensor package is physically separated from the smartphone. The embodiment where the sensor unit is in a separate package, detachable from the smartphone, would also allow for specialized arrangements, such as a sensor wand, transmitting/receiving antenna and a battery power pack to operate the sensor system.

The present invention will include a microcontroller 102 to operate the nanotube sensors and retrieve raw data from the sensors. The microcontroller 102 will send data to the smartphone. The CPU on the smartphone will then be used through a unique application to do the final calculation of sensor output values in typical units, such as, but not limited to, temperature in degrees (e.g., ° C. or ° F.), barometric pressure in bar, relative humidity in percent, gas concentrations in either percent or parts-per-million volume (ppmv).

The data from the sensors can be stored in smartphone memory devices or, for separately housed sensor packages, the data may be stored on a memory chip included in this separate housing. Data may also be transmitted wirelessly, through either a Wi-Fi network or via the smartphone's cellular network, to other locations, such as a plant safety office computer, where the current atmospheric conditions of the user could be recorded and analyzed to determine such things as exposure levels and time of exposure to hazardous gases. The data could also be transmitted to either a community computer or some other computer, such as a cloud-based server, where atmospheric conditions data from numerous individual phone-sensor packages could be recorded, along with location data from each phone's GPS chip. The air quality data and the location data could be coordinated with map data and displays.

Data from the whole plant, or community, or region, including data from a multiplicity of phones, would be collated on this external server/computer and then could be downloaded back to the individual phones to show air quality throughout the plant, community or region. Settings in the mobile electronic device application would be available to limit distribution of data where desired. The plant, community or region data, including the compilation of data from a multiplicity of phones, could also be used as part of a general safety system, such as plant or community warning sirens.

The present invention can range from a smartphone or hand-held radio that replaces other personal safety monitoring devices in plant safety applications to a general use atmospheric and air quality measurement device integrated into a typical smartphone. Data from a multiplicity of such sensor equipped hand-held electronic devices could be made available to each individual device to provide regional information to each user.

This invention combines advanced, low-cost, high-response sensor systems with an existing hand-held device, such as a smartphone or its equivalent, to monitor, record, and transmit data related to air quality and conditions in the locale of the individual using that hand-held device.

In one embodiment, the device would act as part of an individual's personal protective equipment to monitor for hazardous chemical exposure. The CNT sensor array can be specifically tailored to the hazardous gases that are of concern to a specific plant, mine, or other industrial application. The invention would monitor levels of the hazardous gas continuously with a sample rate as fast as 4 samples per second. Sensor information would be shown on the phone's screen through its dedicated application and could also be recorded on the hand-held device. The sensor data could also be transmitted to a central computer or server where it could be integrated with similar data from a multiplicity of these devices. This data can be used in a number of ways, including to:
1. Document exposure levels and durations for each individual.
2. Implement a plant-wide warning system if needed or be used to only notify specific individuals in the immediate vicinity of problems.
3. Send out general notifications to all individuals showing current conditions, relating not just to the hazardous compounds, but to general air quality or atmospheric conditions.
4. Notify surrounding neighborhoods if hazardous leaks have been detected.

In yet another embodiment, the hand-held sensor and monitor device would be used by individuals to monitor outdoor air quality and atmospheric conditions. Sensor information would be shown on the phone's screen through a dedicated application and could also be recorded on the hand-held mobile electronic device. The sensor data could also be transmitted to a central computer or server where it could be integrated with similar data from a multiplicity of these devices. This data can be used in a number of ways, including to:
1. Provide a community, region, or world-wide map of air quality.
2. Notify individuals with specific needs of potentially harmful conditions in specific locations.

In yet another embodiment, or as a modification to the outdoor air quality monitor, the hand-held sensor and monitor device would be used by individuals to monitor indoor air quality. Sensors could be tailored to monitor both outdoor and indoor air quality and to monitor specific gases or compounds of concern for a given individual user. Sensor information would be shown on the smartphone's screen through its dedicated application and could also be recorded on the hand-held device. The sensor data could also be transmitted to a central computer or server where it could be integrated with similar data from a multiplicity of these devices. The data could be used in a number of ways, including to:
1. Provide a building map of air quality useful for evacuation in emergency situations.
2. Link with the building's HVAC system to provide an enhanced "smart" control capability for the system due to the additional data these devices would provide.

In summary, the present invention provides a method of quantifying conditions in the atmospheric air surrounding the device. The sensor system is comprised of nanoscale sensors measuring temperature, humidity, pressure, and gaseous concentrations of $CO$, $CO_2$, $CH_4$, and $O_2$ levels and at rates of up to four times per second. In one embodiment, the sensor package is attached to an existing smartphone through a standard USB type connection and docking system. For this embodiment, the sensor package could be docked or could be physically separated but communicating with the smartphone through a wireless connection. For another embodiment, the sensors are integrated into a smartphone providing the same capability in one package. The data collected from the sensors can be: 1) displayed in an application on the smartphone; 2) stored in smartphone memory or, in one embodiment, on a separate memory storage device; 3) sent via wireless connection (either Wi-Fi, Bluetooth™, or cellular) to a separate storage sever; or 4) any combination of these and other techniques used to collect and store data on a smartphone. For one embodiment, the sensor would act as part of a worker's personal protective equipment where, for this application, the data could be wirelessly transmitted to a control computer which could be located inside a central plant control room or be part of a plant monitoring system where exposure levels could be recorded as a function of time and position. The purpose of this embodiment of the invention is to provide protection to workers and operators inside large plants and, generally, to monitor air quality individuals are exposed to at any given time, both indoor and outdoor. Data from a multiplicity of these hand-held sensor devices that could be transmitted to a separate computer could be collectively integrated and collated and then sent back to each individual device for reporting area, community, plant, or even worldwide air quality information.

Whereas, the invention has been described in relation to the drawings attached hereto, it should be understood that other and further modifications, apart from those shown or suggested herein, may be made within the scope of this invention.

BIBLIOGRAPHY

[1] N. Ames, "Ames Technology Capabilities and Facilities," NASA, [Online]. Available: http://www.nasa.gov/centers/ames/research/technology-onepagers/gas_detection.html.
[2] D. B. G. Ilia N. Ivanov, "Carbon nanotube temperature and pressure sensors," U.S. Pat. Publ. No. 2011/0051775 A1, Mar. 3, 2011.
[3] S. B. P. B. Michael S. Strano, "Sensors employing single-walled carbon nanotubes." U.S. Pat. No. 8,765,488 B2, 1 Jul. 2014.
[4] C. Landorf, "Highly soluble carbon nanotubes with enhanced conductivity." Pat. Publ. No. WO 2012/177975 A1, Dec. 27, 2012.

What is claimed is:
1. A hand-held sensor and monitor system for sensing and monitoring atmospheric air quality, which system comprises:
a plurality of sensors, wherein said plurality of sensors are carbon nanotube-based sensors;

a sensor and monitor system microcontroller in communication with said plurality of sensors to receive data therefrom;

a mobile electronic device in communication with said sensor and monitor system microcontroller capable of receiving data from said sensor and monitor system microcontroller;

wherein said plurality of sensors measure quantitative levels of multiple, different gaseous concentrations, wherein said multiple, different gaseous concentrations measured include carbon monoxide, carbon dioxide, methane, oxygen, nitrogen dioxide, nitrous oxide, sulfur dioxide, hydrogen sulfide, ethane, ammonia, benzene, toluene, xylene, acrolein, formaldehyde, acetaldehyde, and acetonitrile.

2. The hand-held sensor and monitor system as set forth in claim 1 wherein said plurality of sensors and said sensor and monitor system microcontroller are integrated into and within said mobile electronic device.

3. The hand-held sensor and monitor system as set forth in claim 1 wherein said plurality of sensors and said sensor and monitor system microcontroller are attachable to and detachable from said mobile electronic device.

4. The hand-held sensor and monitor system as set forth in claim 3 wherein said plurality of sensors and said sensor and monitor system microcontroller are contained within a hand-held wand.

5. The hand-held sensor and monitor system as set forth in claim 1 wherein said plurality of sensors measure temperature.

6. The hand-held sensor and monitor system as set forth in claim 1 wherein said plurality of sensors measure humidity.

7. The hand-held sensor and monitor system as set forth in claim 1 wherein said mobile electronic device provides analysis of said data and provides displays results of said analysis.

8. The hand-held sensor and monitor system as set forth in claim 7 wherein said displays include area maps or general areawide information results.

9. The hand-held sensor and monitor system as set forth in claim 1 wherein said mobile electronic device includes a database for storing said data from said microcontroller.

10. The hand-held sensor and monitor system as set forth in claim 1 including a control central processing unit capable of communicating with and receiving data from said mobile electronic device.

11. The hand-held sensor and monitor system as set forth in claim 10 wherein said mobile electronic device communicates wirelessly with said control central processing unit.

12. The hand-held sensor and monitor system as set forth in claim 10 wherein a plurality of mobile electronic devices communicate wirelessly with said control central processing unit.

13. The hand-held sensor and monitor system as set forth in claim 12 wherein data from said plurality of mobile electronic devices is integrated and collated and coordinated with map information or general areawide information.

14. The hand-held sensor and monitor system as set forth in claim 1 wherein said data from said plurality of sensors are monitored to generate a hazard alert.

15. The hand-held sensor and monitor system as set forth in claim 1 wherein said mobile electronic device is a smartphone.

16. The hand-held sensor and monitor system as set forth in claim 1 wherein said mobile electronic device is a hand-held radio.

17. A hand-held sensor and monitor system for sensing and monitoring atmospheric air quality, which system comprises:

a plurality of sensors, wherein said plurality of sensors are carbon nanotube-based sensors having a gas sensitive active sensing layer;

a sensor and monitor system microcontroller in communication with said plurality of sensors to receive data therefrom;

a mobile electronic device in communication with said sensor and monitor system microcontroller capable of receiving data from said sensor and monitor system microcontroller;

wherein said plurality of sensors measure quantitative levels of multiple, different gaseous concentrations, wherein said multiple, different gaseous concentrations measured include carbon monoxide, carbon dioxide, methane, oxygen, nitrogen dioxide, nitrous oxide, sulfur dioxide, hydrogen sulfide, ethane, ammonia, benzene, toluene, xylene, acrolein, formaldehyde, acetaldehyde, and acetonitrile.

18. The hand-held sensor and monitor system as set forth in claim 17 wherein said plurality of sensors and said sensor and monitor system microcontroller are integrated into and within said mobile electronic device.

19. The hand-held sensor and monitor system as set forth in claim 17 wherein said plurality of sensors and said sensor and monitor system microcontroller are attachable to and detachable from said mobile electronic device.

20. The hand-held sensor and monitor system as set forth in claim 17 wherein said plurality of sensors and said sensor and monitor system microcontroller are contained within a hand-held wand.

* * * * *